United States Patent [19]

Aigner et al.

[11] Patent Number: 4,954,646

[45] Date of Patent: Sep. 4, 1990

[54] PROCESS FOR THE PREPARATION OF SULFATED ALKANOL OXETHYLATES OR ALKYLPHENOL OXETHYLATES HAVING A LOWERED CONTENT OF 1,4-DIOXANE

[75] Inventors: Rudolf Aigner; Günther Müller, both of Burgkirchen; Rainer Müller; Horst Reuner, both of Burghausen, all of Fed. Rep. of Germany

[73] Assignee: Hoechst Aktiengesellschaft, Frankfurt am Main, Fed. Rep. of Germany

[21] Appl. No.: 305,298

[22] Filed: Feb. 1, 1989

[30] Foreign Application Priority Data

Feb. 3, 1988 [DE] Fed. Rep. of Germany ....... 3803110

[51] Int. Cl.$^5$ .................. C07C 141/02; C07C 141/16
[52] U.S. Cl. ........................................ 558/31; 558/33; 558/34
[58] Field of Search ............................ 558/31, 33, 34

[56] References Cited

U.S. PATENT DOCUMENTS 4,285,881 8/1981 Yang ..................................... 558/31
4,411,815 10/1983 Ando et al. ......................... 252/353

FOREIGN PATENT DOCUMENTS 0052801 6/1982 European Pat. Off. .

OTHER PUBLICATIONS

Derwent Abstract of EP 0052801 (6-1982).
Kociba et al., Toxicol. and Appl. Pharmacol., 30, 275-286 (1974).

*Primary Examiner*—Nicky Chan

[57] ABSTRACT

A process for the preparation of sulfated alkanol oxethylates or alkylphenol oxethylates is described. After completion of the reaction with SO$_3$, 0.1 to 0.5% by weight, relative to the alkanol oxethylates or alkylphenol oxethylates employed, of at least one of the following compounds: water, ethanol, 1-propanol, 2-propanol or n-heptane are admixed to the reaction mixture and liquid and gas are subsequently separated at a temperature of 20° to 60° C. The liquid is then neutralized with aqueous alkali as customary and leads to ether sulfate/water mixtures with considerably reduced contents of 1,4-dioxane which can either be used without further aftertreatment or with a considerably reduced outlay in terms of aftertreatment as personal hygiene agents and for various other purposes.

10 Claims, No Drawings

PROCESS FOR THE PREPARATION OF SULFATED ALKANOL OXETHYLATES OR ALKYLPHENOL OXETHYLATES HAVING A LOWERED CONTENT OF 1,4-DIOXANE

The invention relates to a process for the preparation of sulfated alkanol oxethylates or alkylphenol oxethylates having a lowered content of 1,4-dioxane.

Sulfated alkanol oxethylates or alkylphenol oxethylates are prepared commercially by reacting alkanols or alkylphenols with ethylene oxide and subsequent sulfation of the addition products with agents such as chlorosulfonic acid or sulfur trioxide. In this case, sulfuric acid hemiesters result, which, as a rule, are then immediately neutralized in aqueous solution using alkaline compounds, for example alkali metal hydroxides. The compounds thus prepared, designated by a collective name as "ether sulfates", are useful surfactants for all sorts of areas of use, for example they are also used as personal hygiene agents. In the sulfation of the alkanol oxethylates or alkylphenol oxethylates 1,4-dioxane, inter alia, is formed as by-product. If a reactor of older design is used in the commercially frequently used sulfation with sulfur trioxide, as is still frequently the case, the sulfated oxethylates contain about 0.2 to 0.03% by weight of 1,4-dioxane, depending on their oxethylate content. Modern reactors admittedly make lower 1,4-dioxane contents possible, approximately in the order of magnitude of 0.07 to 0.005% by weight, however this is not sufficient for the requirements of the market for certain uses.

From toxicological investigations by R. J. Kociba et al., Toxicology, Applied Pharmacology, Vol. 30 (1974), pages 275 to 298, it emerges that 1,4-dioxane causes damage to health in animal experiments, however, with the use of very large amounts. Although no direct danger in the processing and use of ether sulfates can be derived from these experiments, since then there has existed in manufacturers and users of ether sulfates, above all in use in the cosmetic area, a great interest in products which, as far as possible, have a substantially reduced content of 1,4-dioxane, in order to exclude any risk. The object therefore exists of lowering the content of 1,4-dioxane in ether sulfates as economically as possible, if possible even in its precursors.

Various methods are known for the reduction of the 1,4-dioxane content in ether sulfates, which all have as their aim a removal of the 1,4-dioxane by heat or steam treatment of the ether sulfate produced. Thus, for example, in U.S. Pat. No. 4,285,881, a process is described to bring ether sulfate/dioxane mixtures into contact with dioxane-free steam, at temperatures from 25° to 150° C., in a stripping device, the ether sulfate/dioxane mixture being used advantageously flowing in a thin layer. According to U.S. Pat. No. 4,411,415, ether sulfates are subjected to heat treatment at 50° to 130° C. under reduced pressure in concentrated 60 to 80% strength by weight aqueous solution, in order to render them odor-free, cyclic ethers (1,4-dioxane) formed in the sulfation as by-products also being removed. In EP No. 52,801-A1, a similar process is described with the directly stated aim of producing ether sulfates having a lowered content of 1,4-dioxane. These processes are complex in terms of apparatus and require not inconsiderable amounts of energy. This outlay could be considerably reduced if the 1,4-dioxane content of the sulfated product were clearly lower even before neutralization than previously customary.

A process has now been found which can be carried out in the existing devices for sulfation with sulfur trioxide without a great additional outlay in terms of apparatus, sulfated products having a clearly reduced content of 1,4-dioxane being formed, so that additional outlay on purification is either unnecessary or can be significantly reduced.

The novel process for the preparation of sulfated alkanol oxethylates or alkylphenol oxethylates, in which at least one liquid alkanol oxethylate or alkylphenol oxethylate is brought into contact, with cooling, with a gas mixture which contains in addition to at least one inert gas, 1 to 8% by volume, relative to the gas mixture, of gaseous $SO_3$, in the ratio of 0.9 to 1 mol of $SO_3$ per mol of OH groups in the alkanol oxethylate or alkylphenol oxethylate, after completion of the reaction the liquid reaction mixture and the gas are separated from one another and the liquid reaction mixture is neutralized using aqueous alkali metal hydroxide, magnesium hydroxide, ammonium hydroxide or substituted ammonium hydroxide, comprises admixing 0.1 to 5% by weight, relative to the alkanol oxethylate or alkylphenol oxethylate employed, of at least one of the following compounds: water, ethanol, 1-propanol, 2-propanol or n-heptane to the reaction mixture after completion of the reaction with $SO_3$, but before the separation of liquid reaction mixture and gas, and the temperature during the separation of liquid and gas being 20° to 60° C.

Alkanol oxethylates which contain 6 to 22 carbon atoms in the alkanol radical are suitable for the process according to the invention. Preferably, those alkanol oxethylates are employed whose alkanol radical has 8 to 18 and, in particular, 10 to 16 carbon atoms. Suitable alkylphenol oxethylates have 1 to 3 alkyl groups bonded to the phenol radical which, in turn, have a total of 8 to 18 carbon atoms.

The number of $-CH_2CH_2O-$ groups in the alkanol oxethylates or alkylphenol oxethylates can vary within wide limits, for example, 1 to 15 such groups can be bonded to an alkanol or alkylphenol radical. Preferably, those compounds are employed in which 1 to 6, and in particular those in which 2 to 4, $-CH_2CH_2O-$ groups are present in the molecule.

The oxethylates are reacted with a gas mixture which in addition to at least one inert gas contains 1 to 8% by volume, relative to the gas mixture, of gaseous $SO_3$, 0.9 to 1 mol of $SO_3$ being used per mol of OH groups in the alkanol oxethylate or alkylphenol oxethylate. Since frequently mixtures of various alkanol oxethylates or alkylphenol oxethylates are reacted with $SO_3$, the amount of $SO_3$ to be used is expediently determined on the basis of the OH number of the oxethylate mixture. In principle, it is possible to use gas mixtures having less than 1% by volume of $SO_3$, but the space-time yield is then decreased unnecessarily. Inert gas mixtures having more than 8% by volume of SO$_3$ in general lead to difficulties due to uneven sulfation, lack of constant temperature and increasing formation of undesired by-products. Preferably, a gas mixture is used which contains 1.5 to 5% by volume, relative to the gas mixture, of gaseous SO$_3$.

Although other inert gases are also suitable, air or nitrogen are preferred, as a rule because of easy availability. The reaction of the liquid ethoxylate or ethoxylate mixture with the SO$_3$-containing inert gas is usually carried out in so-called falling film reactors, in which a liquid film trickling in a thin layer on a cooled wall is brought into contact in a continuous current with the gas. Kettle cascades, for example, would be suitable as further possible reactors. The liquid-gas mixture resulting in the reaction is, as a rule, separated after completion of the reaction in a centrifugal separator (cyclone) into liquid reaction mixture and gas which contains only traces of SO$_3$.

The liquid reaction mixture is then immediately neutralized using aqueous alkali metal hydroxide, magnesium hydroxide, ammonium hydroxide or substituted ammonium hydroxde. Depending on the amount of water employed in this case, water-containing concentrates having an ether sulfate content of up to 80% by weight, relative to the concentrate, or concentrated aqueous solutions having ether sulfate contents of about 15 to about 35% by weight, relative to the concentrated solution, are thus formed. Lower concentrations can, admittedly, be prepared easily, but are disadvantageous because of the comparatively high transport volume.

In addition to unsubstituted ammonium hydroxide, substituted ammonium hydroxides can also be used for neutralization, for example an ammonium hydroxide which is substituted with 1 to 4 alkyl groups which, in turn, can each contain 1 to 4 carbon atoms, ammonium hydroxides substituted with benzyl or hydroxyalkyl groups are also suitable. The latter expediently contain 2 to 4, preferably 2, carbon atoms in the hydroxyalkyl group.

According to the invention, 0.1 to 5% by weight, relative to the alkanol oxethylate or alkylphenol oxethylate employed, of at least one of the following compounds: water, ethanol, 1-propanol, 2-propanol or n-heptane are admixed to the reaction mixture, containing liquid and gas, which is produced after completion of the reaction with SO$_3$, but before the separation of this mixture into gas and liquid and the temperature is adjusted so that it is 20° to 60° C. during the separation of liquid and gas. Water is preferably used because of easy availability and favorable action.

The temperature at which the separation of gas and liquid is carried out is expediently already adjusted during the reaction of SO$_3$ with the alkanol oxethylate or alkylphenol oxethylate, but this reaction can also be run using a lower temperature, in order to prevent the formation of by-products, and the mixture with the previously mentioned additives, for example water, can be brought to the desired temperature only shortly before the separation of gas and liquid. The separating-off effect of 1,4-dioxane is in general too low beneath 20° C., above 60° C. undesired side reactions, for example the formation of additional 1,4-dioxane, commence. Preferably, the separation of gas and liquid takes place at a temperature of 25° to 45° C.

Good results are obtained when 0.2 to 2% by weight, relative to the alkanol oxethylate or alkylphenol oxethylate employed, of at least one of the compounds: water, ethanol, 1-propanol, 2-propanol or n-heptane (subsequently designated "additive" for the sake of brevity) are added to the reaction mixture after the reaction with SO$_3$. Mixtures of two or more additives can also be used. The introduction of the additives or the additive into the reaction mixture usually arriving as a foam with a considerable flow rate is expediently carried out rapidly with good mixing, for example in that the flow rate of the additives is increased by narrowing the passage cross-section. Jets which divide the additive into fine droplets are particularly suitable. The inlet direction of the additive is advantageously chosen so that turbulences are formed in the reaction mixture, the formation of an annular flow perpendicular to the flow direction of the reaction mixture can also have a favourable effect, and if appropriate static mixers or stirrers can be used.

In addition to the additive or additives, 0.5 to 3 parts by volume of at least one inert gas can be added to the reaction mixture per part by volume of the SO$_3$-containing gas mixture employed, after the completion of the reaction with SO$_3$, but before the separation of liquid reaction mixture and gas. Suitable inert gases are, for example, air or nitrogen. The separation of the 1,4-dioxane is frequently even improved by means of this. The addition of the inert gas is expediently carried out similarly to the addition of the additive.

In a preferred embodiment of the process according to the invention, 0.5 to 100 parts by weight per hour, preferably 5 to 50 parts by weight per hour, of the liquid reaction mixture obtained after reaction with SO$_3$ and separation of the gas to 1 part by weight per hour of the alkanol oxethylate or alkylphenol oxethylate employed are cooled, one or more of the abovementioned additives are added in the likewise abovementioned amounts, relative to alkanol oxethylate or alkylphenol oxethylate employed, the mixture is recycled and again mixed with the reaction mixture consisting of liquid and gas after completion of the reaction with SO$_3$.

It is to be borne in mind that in the separation of the gas from the liquid reaction mixture not all the additive is removed as a gas together with 1,4-dioxane, but an equilibrium is established between removed additive and additive remaining in the reaction mixture which, inter alia, is dependent on the temperature and pressure during the separation. The amount of additive remaining in the liquid reaction mixture is expediently determined after establishment of the equilibrium and, if it is water, borne in mind with the amount of water which is added in the neutralization. The additive can be admixed to the cooled recycled liquid in various ways, for example by allowing it to flow in then leading through a static mixer, by stirring in or spraying in.

If, after starting the reaction with $SO_3$, the amount of reaction mixture produced by the separation of the gas begins to exceed the amount required for recycling of the cooled liquid, removal of a part of the liquid reaction mixture and neutralization therefore using the aqueous alkalis described above is begun.

The mean residence time from the addition of the additive or additives to the reaction mixture until the removal of the liquid reaction mixture for neutralization should not exceed 60 minutes, since the reaction mixture which has not yet been neutralized tends to form by-products. Preferably, the mean residence time mentioned is 1 to 30 and, in particular, 2 to 15 minutes. This is to be considered, above all, in the procedure using recycled, cooled reaction mixture.

As already mentioned above, should the temperature in the separation of the liquid reaction mixture and the gas be 20° to 60° C., the separation can be carried out at a pressure of about 10 to about 120 kPa. Pressures below 10 kPa are, in principle, possible and even favorable for the separation of 1,4-dioxane, but in general they demand a no longer justifiable greater outlay in terms of apparatus owing to the additional effect. Pressures over 120 kPa bring no improvement, preferably the reaction is carried out at normal atmospheric pressure.

The gas separated off from the liquid reaction mixture contains vapors from the additive or the additives and the 1,4-dioxane in addition to the inert gases used for the mixture with $SO_3$. In general, recovery of the 1,4-dioxane and also the additives is not profitable, these are expediently washed out, for example using water, and the residual gas is given off into the atmosphere, while the washing water is fed to a biological clarifier. If n-heptane is used, the gas can be fed to an incinerator.

As already mentioned above, the process according to the invention makes it possible to reduce considerably the 1,4-dioxane content of the liquid alkanol oxethylates or alkylphenol oxethylates reacted with $SO_3$ with comparatively low outlay in terms of apparatus and low additional costs, so that the reaction products can often be used after the customary neutralization without further aftertreatment or at least with a substantially reduced outlay on aftertreatment.

The following examples illustrate the invention in more detail:

COMPARISON EXPERIMENT A 1,036 parts by weight per hour of a fatty alcohol oxethylate which on average contains two —$CH_2CH_2O$— groups and has an OH number of 195, a molecular weight of 288 and a carbon chain distribution of the fatty alcohol of $C_{10}=$ about 1%; $C_{12}=54+3\%$, $C_{14}=44+3\%$ and $C_{16}=$about 1%, are brought to reaction with 283 parts by weight per hour of $SO_3$ in the form of a mixture with air containing 2.2% by volume of $SO_3$ in a falling film reactor having a connecting quench space. 0.98 mol of $SO_3$ are employed per mol of OH groups in the fatty alcohol oxethylate. The sulfuric acid hemiester/air mixture leaving the quench space is fed into a cyclone and is separated in the latter into gas and liquid at a temperature of 35° C. under normal atmospheric pressure. When about 230 parts by weight of liquid have collected in the cyclone this liquid is pumped back via a condenser into the quench space of the falling film reactor and intensively mixed therein with the reaction mixture flowing from the falling film reactor by allowing to flow in rapidly. 1,324 parts by weight per hour of liquid essentially containing sulfuric acid hemiester, which has an acid number of 149.7 (theoretical acid number 152.8), are drawn off from the liquid circulation while keeping the 230 parts by weight content of the hydrocyclone constant and fed to the neutralization. The mean residence time of the liquid essentially containing sulfuric acid hemiester between the completion of the reaction with $SO_3$ and the neutralization is 15 minutes. In the neutralization, the liquid essentially containing sulfuric acid hemiester is neutralized using 218 parts by weight per hour of an aqueous sodium hydroxide solution which contains 50% by weight of NaOH, with admixing of 417 parts by weight per hour of water. A water-containing paste is thus obtained which contains 70% by weight, relative to the paste, of ether sulfate. The content of 1,4-dioxane of this paste is determined to be 0.0076% by weight, relative to 100% of ether sulfate. - 35,000 parts by weight per hour of the cooled liquid essentially containing sulfuric acid hemiester are fed back and introduced into the quench space downstream of the falling film reactor, i.e. 33.8 parts by weight per hour of liquid fed back per part by weight per hour of fatty alcohol oxethylate employed.

EXAMPLE 1

The procedure is as indicated in Comparison Experiment A, but 3 parts by weight per hour, i.e. 0.29% by weight of water, relative to the fatty alcohol oxethylate employed, are added to the recycled liquid essentially containing sulfuric acid hemiester, after cooling and after removing the part which passes to the neutralization, and subsequently mixed intensively in a static mixer. The temperature in the separation of liquid and gas is again 35° C. under normal atmospheric pressure. After establishment of the equilibrium, 0.17% by weight of water is determined in the liquid essentially containing sulfuric acid hemiester, which leaves the cyclone. The water added in the neutralization is reduced by a corresponding amount. A content of 1,4-dioxane of 0.0034% by weight, relative to 100% ether sulfate, is determined in the paste containing 70% by weight of ether sulfate thus obtained.

EXAMPLE 2

The procedure is as in Example 1, but 12 parts by weight per hour of water, i.e. 1.2% by weight, relative to the fatty alcohol oxethylate employed, instead of 3 parts by weight per hour, are introduced into the circulation of the cooled liquid essentially containing sulfuric acid hemiester. The content of 1,4-dioxane of the 70% strength by weight aqueous ether sulfate paste is 0.0019% by weight, relative to 100% ether sulfate.

COMPARISON EXPERIMENT B 811 parts by weight per hour of a fatty alcohol oxethylate which on average contains 2 —$CH_2CH_2O$— groups, and has an OH number of 201.8, a molecular weight of 278 and a carbon chain distribution of the fatty alcohol of $C_{10}$=about 1.5%; $C_{12}$=71±3%; $C_{14}$=26 +3% and $C_{16}$=1.5%, are brought to reaction with 226.4 parts by weight per hour of $SO_3$ in the form of a mixture with air containing 1.8% by volume of $SO_3$ in a falling film reactor having a connecting quench space. 0.97 mol of $SO_3$ is employed per mol of OH groups in the fatty alcohol oxethylate. The sulfuric acid hemiester/air mixture leaving the quench space is fed into a cyclone and separated in the latter into gas and liquid at a temperature of 35° C. under normal atmospheric pressure. When about 10 parts by weight of liquid have collected in the cyclone, this liquid is pumped back into the quench space of the falling film reactor via a condenser and intensively mixed therein with the reaction mixture flowing from the falling film reactor by allowing it to flow in rapidly. 1,035 parts by weight per hour of liquid essentially containing sulfuric acid hemiester, which has an acid number of 152.0, is drawn off from the liquid circulation while keeping the 10 parts by weight content of the hydrocyclone constant, and fed to the neutralization.

The average residence time of the liquid essentially containing sulfuric acid hemiester between the completion of the reaction with $SO_3$ and the neutralization is 5 minutes. In the neutralization, the liquid essentially containing sulfuric acid hemiester is neutralized using 227 parts by weight per hour of an aqueous sodium hydroxide solution which contains 50% by weight of NaOH, while admixing 2,680 parts by weight of water per hour. An aqueous solution is obtained which contains 28% by weight of ether sulfate, relative to the aqueous solution. The content of 1,4-dioxane is determined from this aqueous solution to be 0.0083% by weight, relative to 100% of ether sulfate. - 35,000 parts by weight per hour of the cooled liquid essentially containing sulfuric acid hemiester are fed back and introduced into the quench space downstream of the falling film reactor, i.e. 43.1 parts by weight per hour of liquid fed back per part by weight per hour of fatty alcohol oxethylate employed.

EXAMPLE 3

The procedure is as indicated in Comparison Example B, but 15 parts by weight per hour, i.e. 1.85% by weight of water, relative to the fatty alcohol oxethylate employed, are added to the recycled liquid essentially containing sulfuric acid hemiester, after cooling and after removing the part which passes to the neutralization, and subsequently mixed intensively in a static mixer. The temperature in the separation of liquid and gas is again 35° C. under normal atmospheric pressure. After establishment of the equilibrium, 0.7% by weight of water is determined in the liquid essentially containing sulfuric acid hemiester which leaves the cyclone. The water added in the neutralization is reduced by a corresponding amount. A content of 1,4-dioxane of 0.0017% by weight, relative to 100% ether sulfate, is determined in the solution containing 28% by weight of ether sulfate thus obtained.

COMPARISON EXAMPLE C

The procedure is as in Comparison Example B, with the following differences:

955 parts by weight per hour of a fatty alcohol oxethylate which on average contains 3 —$CH_2CH_2O$— groups, and has an OH number of 173, a molecular weight of 324 and a carbon chain distribution of the fatty alcohol of $C_{10}$=about 1%; $C_{12}$=54±4%; $C_{14}$=44±3% and $C_{16}$=about 1%, are brought to reaction with 226.4 parts by weight per hour of $SO_3$ in the form of a mixture with air containing 1.8% by volume of $SO_3$. 0.97 mol of $SO_3$ is employed per mol of OH groups in the fatty alcohol oxethylate. To neutralize the sulfuric acid hemiester, 227 parts by weight per hour of an aqueous sodium hydroxide solution which contains 50% by weight of NaOH and 373 parts by weight per hour of water are used. The aqueous ether sulfate paste thus obtained has a content of 1,4-dioxane of 0.0167% by weight, relative to 100% of ether sulfate.

As in Comparison Example B, 35,000 parts by weight per hour of the cooled liquid essentially containing sulfuric acid hemiester are fed back and introduced into the quench space downstream of the falling film reactor, i.e. 36.6 parts by weight per hour of liquid fed back per part by weight per hour of fatty alcohol oxethylate employed.

EXAMPLE 4

The procedure is as indicated in Comparison Experiment C, but 10 parts by weight per hour, i.e. 1.05% by weight of water, relative to the fatty alcohol oxethylate employed, are added to the recycled liquid essentially containing sulfuric acid hemiester, after cooling and after removing the part which passes to the neutralization, and subsequently mixed intensively in a static mixer. The temperature in the separation of liquid and gas is 35° C. under normal atmospheric pressure. After establishment of the equilibrium, 0.45% by weight of water is determined in the liquid essentially containing sulfuric acid hemiester, which leaves the cyclone. A content of 1,4-dioxane of 0.0066% by weight, relative to 100% ether sulfate, is determined in the aqueous ether sulfate paste obtained after the neutralization.

COMPARISON EXPERIMENT D

The procedure is as described in Comparison Experiment C, but the $SO_3$ is employed as a 3.8% strength by volume mixture with air. The liquid-gas mixture essentially containing sulfuric acid hemiester emerging from the reactor system is separated in a cyclone and 70,000 parts by weight per hour, i.e. 73.3 parts by weight per hour per part by weight per hour of alcohol oxethylate employed, of the liquid, freed from gas, essentially containing sulfuric acid hemiester, are recycled via a condenser into the quench space arranged downstream of the reactor. The average residence time of the liquid essentially containing sulfuric acid hemiester between the completion of the reaction with $SO_3$ and the neutralization is 5 minutes. The temperature in the separation of the liquid from the gas is 30° C. 1,190 parts by weight per hour of the liquid essentially containing sulfuric acid hemiester are removed and neutralized using 227 parts by weight per hour of an aqueous sodium hydroxide solution containing 50% by weight of NaOH and 373 parts by weight per hour of water. The 1,4-dioxane content of the ether sulfate paste obtained after the neutralization is 0.0123% by weight, relative to 100% of ether sulfate.

EXAMPLE 5

The procedure is as indicated in Comparison Experiment D, but 10 parts by weight per hour, i.e. 1.04% by weight of water, relative to the fatty alcohol oxethylate employed, are added to the recycled liquid essentially containing sulfuric acid hemiester, after cooling and after removing the part which passes to the neutralization, and subsequently mixed intensively in a static mixer. The temperature in the separation of liquid and gas is 30° C. under normal atmospheric pressure. After establishment of the equilibrium, 0.9% by weight of water is determined in the liquid essentially containing sulfuric acid hemiester which leaves the cyclone. The water added in the neutralization is reduced by a corresponding amount. A content of 1,4-dioxane of 0.0023% by weight, relative to 100% of ether sulfate, is determined in the ether sulfate paste thus obtained.

COMPARISON EXPERIMENT E

The procedure is as in Comparison Experiment A, but 20,000 parts by weight per hour of the cooled liquid essentially containing sulfuric acid hemiester are fed back and introduced into the quench space downstream of the falling film reactor, i.e. 19.3 parts by weight of liquid fed back per part by weight of fatty alcohol oxethylate employed. The temperature in the separation of liquid and gas is 30° C. under normal atmospheric pressure. The neutralization is carried out as described in Comparison Experiment A. An aqueous paste is thus obtained which contains 70% by weight, relative to the paste, of ether sulfate. The content of 1,4-dioxane of this paste is determined to be 0.0050% by weight, relative to 100% of ether sulfate.

EXAMPLE 6

The procedure is as indicated in Comparison Experiment E, but 19.5 parts by weight per hour, i.e. 1.9% by weight of water, relative to fatty alcohol oxethylate employed, are added via a jet to the recycled liquid essentially containing sulfuric acid hemiester and subsequently mixed intensively in a static mixer. The temperature in the separation of liquid and gas is again 30° C. under normal atmospheric pressure. After establishment of the equilibrium, 0.7% by weight of water is determined in the liquid essentially containing sulfuric acid hemiester which leaves the cyclone. The water added in the neutralization is reduced by a corresponding amount. A content of 1,4-dioxane of 0.0008% by weight, relative to 100% of ether sulfate, is determined in the ether sulfate paste thus obtained.

We claim:

1. A process for the preparation of sulfated alkanol oxethylates or alkylphenol oxethylates, in which at least one liquid alkanol oxethylate or alkylphenol oxethylate is brought into contact, with cooling, with a gas mixture which contains in addition to at least one inert gas, 1 to 8% by volume, relative to the gas mixture, of gaseous $SO_3$, in the ratio of 0.9 to 1 mol of $SO_3$ per mol of OH groups in the alkanol oxethylate or alkylphenol oxethylate, after completion of the reaction the liquid reaction mixture and the gas are separated from one another and the liquid reaction mixture is neutralized using aqueous alkali metal hydroxide, magnesium hydroxide, ammonium hydroxide or substituted ammonium hydroxide, which comprises admixing 0.1 to 5% by weight, relative to the alkanol oxethylate or alkylphenol oxethylate employed, of at least one of the following compounds: water, ethanol, 1-propanol, 2-propanol or n-heptane to the reaction mixture after completion of the reaction with $SO_3$, but before the separation of liquid reaction mixture and gas, and the temperature during the separation of liquid and gas being 20° to 60° C.

2. The process as claimed in claim 1, in which 0.5 to 100 parts by weight per hour of the liquid reaction mixture obtained after reaction with $SO_3$ and separation of the gas to 1 part by weight per hour of the alkanol oxethylate or alkylphenol oxethylate employed are cooled, recycled and added to the reaction mixture consisting of liquid and gas after completion of the reaction with $SO_3$, wherein at least one of the compounds mentioned in claim 1 is admixed to this recycled liquid reaction mixture.

3. The process as claimed in claim 1, wherein water is employed as the admixed compound.

4. The process as claimed in claim 1, wherein 0.2 to 2% by weight, relative to the alkanol oxethylate or alkylphenol oxethylate employed, of at least one of the compounds mentioned in claim 1 are added to the reaction mixture.

5. The process as claimed in claim 1, wherein the temperature in the separation of liquid reaction mixture and gas is 25° to 45° C.

6. The process as claimed in claim 1, wherein at least one alkanol oxethylate is employed which contains 8 to 18 carbon atoms in the alkanol moiety.

7. The process as claimed in claim 1, wherein at least one alkanol oxethylate or alkylphenol oxethylate which contains 1 to 6 —$CH_2CH_2O$— groups is used.

8. The process as claimed in claim 1, wherein a gas mixture is used which contains 1.5 to 5% by volume, relative to the gas mixture, of gaseous $SO_3$.

9. The process as claimed in claim 1, wherein the mean residence time from the addition of the compounds mentioned in claim 1 to the reaction mixture until neutralization is 1 to 30 minutes.

10. The process as claimed in claim 1, wherein 0.5 to 100 parts by volume of at least one inert gas are added to the reaction mixture per part by volume of the $SO_3$-containing gas mixture employed, after the completion of the reaction with $SO_3$, but before the separation of liquid reaction mixture and gas.

* * * * *